United States Patent [19]

Kross et al.

[11] Patent Number: 5,019,402

[45] Date of Patent: May 28, 1991

[54] COMPOSITION AND PROCEDURE FOR DISINFECTING BLOOD AND BLOOD COMPONENTS

[75] Inventors: Robert D. Kross, Bellmore, N.Y.; David I. Scheer, Guilford, Conn.

[73] Assignee: Alcide Corporation, Norwalk, Conn.

[21] Appl. No.: 483,205

[22] Filed: Feb. 20, 1990

Related U.S. Application Data

[63] Continuation-in-part of Ser. No. 230,785, Aug. 10, 1988, abandoned.

[51] Int. Cl.$^5$ ............................................. A61K 35/16
[52] U.S. Cl. ..................................... 424/665; 424/661; 424/531; 424/532; 424/534; 424/663; 435/2; 422/37
[58] Field of Search ............... 424/529, 530, 531, 532, 424/533, 534, 661, 663, 665; 435/2; 422/37

[56] References Cited

U.S. PATENT DOCUMENTS

| | | | |
|---|---|---|---|
| 4,084,747 | 4/1978 | Alliger | 422/37 |
| 4,725,437 | 2/1988 | Kuhne | 424/661 |

FOREIGN PATENT DOCUMENTS

| | | | |
|---|---|---|---|
| 88/4107 | 9/1985 | PCT Int'l Appl. | 424/661 |
| 88/1507 | 3/1988 | PCT Int'l Appl. | |

Primary Examiner—Douglas W. Robinson
Assistant Examiner—Jean Witz
Attorney, Agent, or Firm—Seed and Berry

[57] ABSTRACT

There is disclosed a composition and process for disinfecting or essentially sterilizing blood fractions and components of blood. The composition is formed by adding a chlorine dioxide liberating compound with a weak organic acid and a heat activated saccharide.

8 Claims, 1 Drawing Sheet

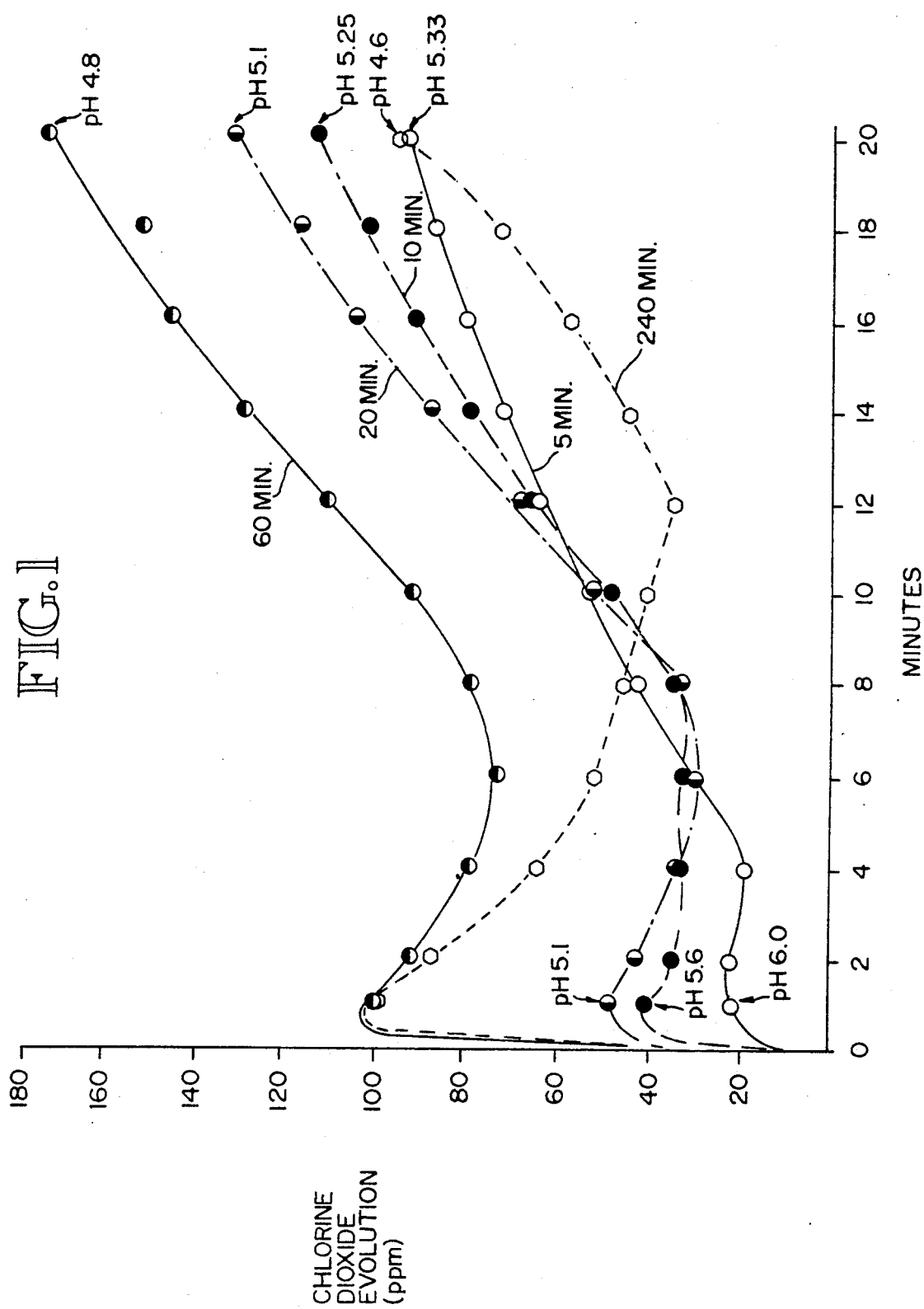

COMPOSITION AND PROCEDURE FOR DISINFECTING BLOOD AND BLOOD COMPONENTS

RELATED APPLICATION

This application is a continuation-in-part of copending U.S. Ser. No. 230,785, filed Aug. 10, 1988 now abandoned.

DESCRIPTION

1. Technical Field

The present invention relates to compositions and to procedures for in vitro disinfection of blood fractions and components of blood. More specifically, this invention relates to in vitro procedures and compositions for disinfecting components of blood such as blood cells, blood proteins, and other fractions isolated from blood.

2. Background of the Invention

Blood and blood components are susceptible to infection from various infectious agents, such as bacteria, viruses, spores, and fungi. Infection of blood or blood components that are isolated, stored, and later used for therapeutic agents or treatment purposes is an important problem in the practice of medicine. Despite the availability of therapeutic agents such as antibiotics and diagnostic assays for the detection of pathogen-associated antibodies and antigens in units of blood, there has not been a satisfactory solution to safeguarding the supply of blood and blood components from infection. A process has been developed by scientists at the New York Blood Center for the inactivation of viruses in certain noncellular fractions of blood (e.g., clotting factor VIII). This approach, however, has not proven applicable to the treatment of the formed elements of blood, such as blood cells.

Antibiotics, other pharmaceuticals, and immunological reagents, when used alone or in combination, do not have the broad spectrum of biocidal activity necessary to be effective against all known and unknown pathogens, including bacteria, viruses, spores, and fungi that can infect blood and blood components. A further problem with therapeutic agents, specifically chemical-based pharmaceutical agents, is the high likelihood that effective concentrations of the agent will also be toxic to blood cells or inhibit the activity of blood protein components.

The problem of the HIV retrovirus contamination is of paramount concern because of reports of HIV contamination of whole blood and blood components when the blood is obtained from an individual infected with the HIV virus. Sarin et al., "Inactivation of Human T-Cell Lymphotropic Retrovirus (HTLV-III) by LD ™," *New England J. of Med.*, 313:1416 (1985), refers to the in vitro inactivation of HTLV-III virus in a cell culture system at a 200-fold dilution of a solution of 0.23% sodium chlorite and 1.26% lactic acid.

Platelet transfusions are a known source of microbial contamination, periodically causing bacterial septicemia. Arnow et al., "*Escherichia coli* Sepsis From Contaminated Platelet Transfusion," *Arch. Int. Med.* 246:321 (1986), reports the use of septic shock secondary to receipt of platelets in a post-chemotherapy patient for acute myelogenous leukemia (AML). The causative agent was identified as *E. coli*. The donor claimed to be in good health.

Platelets are obtained from whole blood by separation procedures. Subsequently, the plasma may be removed and replaced with platelet storage medium. Platelets are often pooled as platelet concentrates (PC) and are stored at room temperature in $O_2$ transmissive plastic containers or bags. Often polyolefin bags are used for storage. The use of $O_2$ transmissive plastic storage bags allows platelets to be stored for more than three days to at least seven days. However, the ability to increase platelet storage time also increases the possibility of overgrowth by initial inocula of contaminating micro-organisms.

Braine et al., "Bacterial Sepsis Secondary to Platelet Transfusion: An Adverse Effect of Extended Storage At Room Temperature," *Transfusion* 26:391 (1986), reports four cases of platelet transfusion-related sepsis at Johns Hopkins Hospital during a two-month period in 1985. All the cases involved platelet concentrates (PC) stored at room temperature, and containing at least one unit stored 5 days or longer. The units were stored in either a polyolefin bag or a PVC (polyvinyl chloride) bag. Three patients had AML and white cell counts (WBC) of 0–3500 and were on cancer chemotherapy and prophylactic antibiotics. The cultures grew *Staphylococcus epidermidis* in one case, *Streptococcus viridans* in another, and both *Staphylococcus epidermidis* and *flavobacterium* in a third case. A fourth patient had ALL (acute lymphocytic leukemia), WBC's of 2300, had undergone bone marrow transplantation and was not on antibiotics. The fourth patient developed septic shock and the organism was identified as *S. epidermidis*.

Braine et al. conclude that prolonged room temperature storage of platelets was the risk in the four reported cases, because Hopkins had not previously experienced platelet transfusion-related infections and because extended platelet storage was introduced at Hopkins when the platelet age went from a maximum of three days to a median age of 4.9 days.

Braine et al. performed a prospective study of bacterial growth in stored platelet bags. The researchers introduced two isolates of *S. epidermidis* into PC bags in inoculates of 1, 7, and 55 organisms per bag. After 72 hours, bacterial cell counts were 3 to 8 logs of organisms per 0.1 ml of PC. After 6 days all bags contained 7 to 8 logs of organisms per 0.1 ml. A strain of Corynebacterium tested with a 230 organism inoculate greW to 142 organisms per 0.1 ml after 7 days at room temperature. Braine et al. recommend that platelet storage time be reduced to a maximum of 5 days.

Accordingly, there exists a need in the art to increase platelet storage time by preventing microbial growth with small inoculum of microbial contamination.

The use of various disinfecting and sterilizing compounds to disinfect a variety of solutions and surfaces is known in the art. For example, chlorine compounds have been used for this purpose. Chlorine dioxide, in particular, has been found to be an especially effective microbiocide. This compound is quite versatile and has been used as a bleaching agent, such as in the oxidation of natural colorant present in cotton, wood pulp, and other cellulosic fiber materials. In these uses, the chlorine dioxide oxidizes the treated material yet is not injurious to the fibrous material. Chlorine dioxide has also been used in the treatment of water supplies and is generally considered to be at least as effective as, if not superior to, chlorine gas as a bactericide, sporicide, fungicide, and virucide.

Sodium chlorite has been found to form a particularly effective germ-killing composition when combined with lactic acid. For example, U.S. Pat. No. Re. 31,779, to Alliger, refers to germ-killing compositions and methods which employ sodium chlorite and lactic acid in an aqueous solution. U.S. Pat. No. 4,330,531 refers to various germ-killing materials, such as gels, toothpastes, and soaps, which are prepared using sodium chlorite and lactic acid as the active germ-killing ingredients.

Chlorine dioxide is an explosive material as a concentrated gas. Its practical applications, however, have been mostly in dilute aqueous solutions. Chlorine dioxide has excellent germ-killing properties with respect to bacteria, fungi, spores, and viruses. More particularly, chlorine dioxide has exhibited germ-killing properties against both gram-positive and gram-negative bacteria, spores from bacteria, molds, yeasts, and viruses.

The search has continued for new and improved biocidal compositions which are both effective at significantly reducing or eliminating bacterial, viral, spore, or fungal contamination of blood fractions and blood components and additionally are not toxic to blood cells or blood proteins. This invention was made as a result of this search.

SUMMARY OF THE INVENTION

Accordingly, a general object of this invention is to avoid or substantially alleviate the above-noted problems in the art.

A more specific object of this invention is to provide a composition and a process for disinfecting blood and blood components without causing undue toxic side effects to blood cells and the activity of blood proteins.

It is a further object of this invention to provide active solutions of chlorine dioxide that are nontoxic or nondisruptive of blood cell membranes and, therefore, are nontoxic to blood cells.

Another object of this invention is to provide a novel process and a novel composition for producing and containing chlorine dioxide as the active therapeutic agent to disinfect and/or to sterilize blood fractions or partially purified blood components, such as globulins, fibrinogen, blood clotting factors, and platelets, in order to remove contaminant pathogens, such as bacteria, viruses, fungi, and spores.

Other objects and advantages of the invention will become known from the following summary of the invention and description of its preferred embodiments.

The present invention provides a novel process and a novel composition that provide an effective and nontoxic means to disinfect blood fractions, such as platelets and blood components that is urgently needed in medical care.

One process for disinfecting blood fractions or blood components comprises adding chlorine dioxide to blood fractions or a blood component solution. Preferably, the process for disinfecting blood or blood components comprises adding a chlorine dioxide liberating compound to a vicinal polyhydroxy compound in a weak organic acid buffer to form a disinfecting solution, diluting the disinfecting solution with an aqueous solution to a concentration of chlorine dioxide within the range of from about 50 ppm to about 1500 ppm, and adding the diluted disinfecting solution to blood fractions, blood cells or a solution of blood components wherein the final concentration of chlorine dioxide in the solution containing blood fractions or blood components is within the range of from about 6 ppm to about 225 ppm. Preferably, the vicinal polyhydroxy compound is dextrose or another five- or six-carbon sugar used as a component of, or in combination with a citrate phosphate (CPD) buffer or acid citrate buffer (ACD). Most preferably, the CPD or ACD buffer with sugar has been heated above 75° C., such as by autoclaving.

The composition for disinfecting blood fractions or blood components comprises a means for adding chlorine dioxide to blood cells or to a solution of blood components. Preferably, the composition for disinfecting blood fractions or blood components comprises an aqueous solution comprising a chlorine dioxide liberating compound and a vicinal polyhydroxy compound in a weak organic acid buffer. The aqueous solution is diluted to a concentration of chlorine dioxide within the range of from about 50 ppm to about 1500 ppm. It is standard practice to have the disinfecting solution consist of approximately 14% of the solution comprising blood fractions or blood components and the disinfecting solution. Preferably, the vicinal polyhydroxy compound contained in a weak organic acid buffer is the dextrose which is already present in the CPD buffer or another five- or six-carbon sugar. Most preferably, the sugar in the buffer is sterilized by heating, such as with an autoclave. It has been shown that the heating of the sugar, such as through heat sterilization, activates the sugar to more effectively catalyze the conversion to chlorine dioxide from the chlorine dioxide liberating compound.

BRIEF DESCRIPTION OF THE DRAWING

The FIGURE illustrates the effect of heating a polyhydroxy compound of the present invention on the rate of release of chlorine dioxide by the chlorine dioxide liberating compound.

DETAILED DESCRIPTION OF THE INVENTION

Briefly stated, the composition of the present invention comprises a means for adding chlorine dioxide to blood cells or to a solution of blood components. The means for adding chlorine dioxide can include the direct addition of chlorine dioxide in gaseous or liquid form to blood cells (fractions) or a blood component solution. Preferably, the means for adding chlorine dioxide to the blood cells or a solution of blood components comprises a chlorine dioxide liberating compound and a vicinal polyhydroxy compound in a weak organic buffer. Examples of chlorine dioxide liberating compounds include any compounds which, when appropriately treated, will liberate chlorine dioxide. Water-soluble chlorites are preferred. Typical water-soluble chlorites include alkali metal chlorites and alkaline earth metal chlorites. Sodium chlorite and potassium chlorite are preferred. Sodium chlorite is particularly preferred.

The vicinal polyhydroxy compound functions to maximally liberate chlorine dioxide from the chlorine dioxide liberating compound. It is preferred that the vicinal polyhydroxy compound be heated to "activate" its catalytic function. The vicinal polyhydroxy compound is preferably heat activated prior to the addition of the chlorine dioxide liberating compound. This heat activation takes place at a temperature of generally at least about 50° C., typically about 60° C. to about 150° C., and preferably from about 75° C. to about 110° C.

The amount of chlorine dioxide gas which evolves is dependent upon the amount of time the vicinal polyhydroxy compound is held at the elevated temperature. This period of time varies depending upon the temperature at which the heat activation is carried out, but the time is generally at least about 1 minute, typically from about 5 to about 240 minutes, and preferably from about 20 to about 120 minutes. These relationships are illustrated graphically in the FIGURE.

The preferred chlorine dioxide liberating compounds, sodium chlorite and potassium chlorite, are relatively toxic to blood cells and blood components. Accordingly, the inventive process minimizes blood cell and blood component toxicity by maximally converting sodium chlorite, potassium chlorite, or other toxic chlorine dioxide liberating compounds to chlorine dioxide, thus minimizing blood cell or blood component exposure.

Examples of vicinal polyhydroxy compounds include glucose, galactose, mannose, ribose, rhamnose and disaccharides, such as lactose and maltose. Preferably, the vicinal polyhydroxy compound has been heated, such as by sterilizing in an autoclave. The vicinal polyhydroxy compound is also nontoxic to the blood cells or blood components.

The polyhydroxy compound, such as a sugar, should first be heated to yield a component which is capable of liberating chlorine dioxide. Preferably, a blood bag with heat-sterilized CPD or ACD is used and the chlorine dioxide liberating compound, such as sodium chlorite, is added to the blood bag followed by the addition of blood fractions or blood components. The reaction of heat-sterilized CPD or ACD and sodium chlorite maximally liberates chlorine dioxide and minimizes the toxic effect of sodium chlorite on blood cells or blood components. The resulting solution can effectively inactivate viruses, such as the HIV virus, in mixtures of blood cells or blood components. Further, the resulting solution can eliminate small inocula of bacteria, yeast or fungi from growing in a blood fraction, such as platelets during storage. The net result is the ability to store blood fractions and blood components for longer periods of time without the risk of microbial overgrowth.

Examples of weak organic acid buffers include combinations of the acids and salts of citric, malic, lactic, mandelic, and tartaric acid. In general, the weak organic acid has the formula:

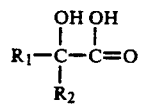

wherein $R_1$ and $R_2$ may be the same or different and may be selected from the group consisting of hydrogen, methyl, $-CH_2COOH$, $-CH_2OH$, $-CHOHCOOH$ and $-CH_2C_6H_5$. Other examples of weak organic acids with a pK of from about 2.8 to about 4.2 are found in U.S. Pat. application No. 850,009 filed Apr. 10, 1986 and incorporated by reference herein.

One distinct advantage of the present invention is the ability to add a chlorine dioxide liberating compound, such as sodium chlorite, to a blood collection bag. Blood collection bags already contain the autoclaved CPD or ACD anticoagulants. Thus, blood cells and components collected in a blood collection bag can be disinfected with the addition of sodium chlorite.

The blood cells or blood components are disinfected in a substantially nontoxic manner. The half-life survival of red blood cells of baboons was investigated after baboon whole blood was treated in vitro using the inventive composition (CPD or ACD and sodium chlorite). No adverse effects were noted when Factor VIII and Factor IX activities were measured, nor were any changes noted in hemoglobin or red blood cell survival. Accordingly, in vitro treatment according to the inventive process of baboon whole blood resulted in no detectable toxic effects.

Examples of blood components are leukocytes (i.e., white cells), platelets and coagulation factors, including Factor VIII, Factor IX and Factor VII, and globulins.

The novel treatment of blood cells and blood components can be applied, for instance, to disinfect fractionated platelets obtained from human and other mammalian blood sources. The treatment with the composition of the present invention can serve to prevent the transmission of viruses, bacteria, and protozoa that are not apparent in the donor but virulent and disease-causing in the recipient individual.

Moreover, while sodium chlorite is known to have an adverse effect on blood cell integrity and functionality, blood factors or platelet viability are not significantly affected by treatment with sodium chlorite using the inventive compositions and processes. It is believed this is because the chlorite is converted by the inventive composition and process to chlorine dioxide, which is better tolerated by the cells.

It is another embodiment of the present invention to sterilize or disinfect blood cells or blood components by utilizing preformed chlorine dioxide rather than a chlorine dioxide liberating composition in solution. Disinfection can be achieved by bringing the chlorine dioxide source in a semipermeable or permeable container into direct contact with the blood cells or blood components to allow disinfection to proceed with an appropriate dosage and over an appropriate time period. For example, this can be achieved by gaseous diffusion of the chlorine dioxide from a solid in a polymer (e.g., polycarbonate) into an aqueous liquid containing blood cells or blood components. The permeability of the container regulates the amount of chlorine dioxide coming into contact with the blood or blood component source.

The present invention is further illustrated by the following examples. The following examples are offered as an illustration and not a limitation of the present invention.

EXAMPLE 1

This example illustrates the amount of log microbial kill of the inventive process when a sample is inoculated with an extremely large amount of bacteria.

A bacterially contaminated platelet suspension is treated with a composition of the present invention. The composition is formed with 0.015% (w/v) sodium chlorite, plus CPD (0.30% (w/v) citric acid, 2.31% (w/v) sodium citrate, 0.193% (w/v) sodium dihydrogen phosphate, and 2.32% (w/v) dextrose) having a pH of about 5.5 and previously heat sterilized. The composition is incubated at room temperature for one hour to create the activated solution of chlorine dioxide. The platelet suspension is made by mixing six parts of washed platelet suspension in CPD buffer enriched with 0.5% (w/v) plasma at pH 7.1. The platelet suspension is bacterially contaminated and then mixed with one part of the activated sodium chlorite solution diluted 1:10 in CPD buffer at a pH of 7.1 to 7.4 and left to stand at room temperature for one hour.

Approximately $5 \times 10^6$ colony-forming units (cfu) of S. aureus and $5 \times 10^6$ cfu of E. coli are added to the platelet suspension to contaminate the platelets. When the activated sodium chlorite solution is added to the contaminated platelet suspension, a 96% reduction in bacterial count of *S. aureus* is achieved. Similarly, when the platelet suspension contaminated with *E. coli* is disinfected with activated sodium chlorite, a decrease om approximately 4 log values of bacterial count is achieved. These data are illustrated in Table 1 where columns A and C are tests in which sodium chlorite is added, while columns B and D represent tests in which no sodium chlorite is added.

TABLE 1

| Sample | S. aureus Count A (cfu) | | B | E. coli Count C (cfu) | | D |
|---|---|---|---|---|---|---|
| Experiment 1 | | | | | | |
| Control saline | 0 | | $4.0 \times 10^6$ | 0 | | $4.1 \times 10^6$ |
| Platelets/5% plasma in artificial media | $2.7 \times 10^5$ | | $4.4 \times 10^6$ | $7.0 \times 10^2$ | | $5.1 \times 10^6$ |
| 20% plasma in artificial media | $1.2 \times 10^6$ | | $5.4 \times 10^6$ | $1.3 \times 10^2$ | | $2.4 \times 10^6$ |
| Experiment 2 | | | | | | |
| Control saline | $1.5 \times 10^1$ | | $1.4 \times 10^6$ | 0 | | $1.0 \times 10^6$ |
| Platelets/5% plasma in artificial media | $6.0 \times 10^1$ | | $4.0 \times 10^6$ | $2.0 \times 10^2$ | | $2.1 \times 10^6$ |
| 20% plasma in artificial media | $4.0 \times 10^2$ | | $3.4 \times 10^6$ | $1.7 \times 10^3$ | | $1.3 \times 10^6$ |

EXAMPLE 2

This example illustrates the lack of toxicity of the inventive process on the biological activity of clotting Factor VIII.

A solution of Clotting Factor VIII (anti-hemophilic factor, AHF) is contaminated in vitro with vesicular stomatitis virus (VSV). A solution of 0.79% (w/v) lactic acid, 1.6% (w/v) sodium chlorite and 1.5% (w/v) sodium EDTA is added to the Clotting Factor VIII contaminated with VSV solution and incubated for one hour. The amount of VSV virus in the solution declined by more than 3.5 log values. The Clotting Factor VIII protein loses minimal biological activity during this treatment.

EXAMPLE 3

This example illustrates how the inventive process can substantially completely sterilize a blood cell or blood component sample when inoculated with a small number of microbial contaminants as can occur in a clinical setting.

The effect of inoculating platelets with *E. coli* is determined with different doses of chlorine dioxide. A 10 ml platelet concentrate is taken to a volume of 50 ml of Plasmalyte, a synthetic platelet storage medium. The platelets were inoculated with 78 to 148 colony-forming units (cfu) of *E. coli*, as shown in Table 2. The platelets are stored in oxygen transmissive bags at room temperature (e.g., 22° C.) and the bacterial counts are taken at days 0, 1, 5 and 7. Chlorine dioxide is added shortly after the inoculum at concentrations of 0 (control), 33 ppm, 50 ppm, 75 ppm, 100 ppm, 125 ppm and 250 ppm. The results, expressed in colony-forming units per ml, are set forth in Table 2.

TABLE 2

| cfu | Dose | Day 0 | Day 1 | Day 5 | Day 7 |
|---|---|---|---|---|---|
| 148 | control | 1.5 | $2.34 \times 10^5$ | $1.90 \times 10^8$ | $1.27 \times 10^8$ |
| 148 | 33 ppm | 1.0 | $1.47 \times 10^4$ | $2.30 \times 10^8$ | $1.66 \times 10^8$ |
| 82 | control | 1.0 | $7.30 \times 10^7$ | $1.75 \times 10^8$ | $1.73 \times 10^8$ |
| 82 | 33 ppm | 6.5 | $4.90 \times 10^5$ | $3.30 \times 10^8$ | $3.25 \times 10^8$ |
| 128 | control | 1.0 | $1.85 \times 10^7$ | $2.62 \times 10^8$ | $1.76 \times 10^8$ |
| 128 | 33 ppm | 0.0 | $2.42 \times 10^8$ | $2.11 \times 10^8$ | $1.60 \times 10^8$ |
| 87 | control | 1.0 | $2.20 \times 10^7$ | $7.80 \times 10^7$ | $8.70 \times 10^7$ |
| 87 | 33 ppm | 0.0 | $7.90 \times 10^6$ | $1.32 \times 10^8$ | $1.09 \times 10^8$ |
| 93 | control | 0.0 | $2.15 \times 10^8$ | $3.82 \times 10^8$ | $3.66 \times 10^8$ |
| 93 | 33 ppm | 1.0 | $3.40 \times 10^7$ | $1.62 \times 10^8$ | $1.67 \times 10^8$ |
| 97 | 50 ppm | 0.0 | 4.0 | $1.50 \times 10^8$ | $2.31 \times 10^8$ |
| 97 | 75 ppm | 0.0 | 0.0 | 0.0 | 0.0 |
| 97 | 100 ppm | 0.0 | 0.0 | 0.0 | 0.0 |
| 78 | 50 ppm | 0.0 | $2.7 \times 10^3$ | $2.42 \times 10^8$ | $2.26 \times 10^8$ |
| 78 | 75 ppm | 0.0 | 0.1 | $2.20 \times 10^8$ | $2.34 \times 10^8$ |
| 87 | 125 ppm | 0.0 | 0.0 | 0.0 | 0.0 |
| 87 | 250 ppm | 0.0 | 0.0 | 0 0 | 0.0 |
| 93 | 125 ppm | 0.0 | 0.0 | 0.0 | 0.0 |
| 93 | 250 ppm | 0.0 | 0.0 | 0.0 | 0.0 |

As can be seen, if any *E. coli* remain viable after the initial exposure to the chlorine dioxide, there is overgrowth of the micro-organism by day 5. All of the 100 ppm, 125 ppm and 250 ppm doses result in initial sterilization, while only one of the two 75 ppm doses is able to sterilize the sample.

EXAMPLE 4

This example illustrates the inability of the inventive process to sterilize whole blood with a large fraction of red blood cells present.

Whole blood is collected in blood bags with heat sterilized CPD previously added to the blood bags. Chlorine dioxide is formed by adding sodium chlorite to the blood bag just prior to the whole blood collection. The addition of sodium chlorite does not materially affect the microbial count. A whole blood sample containing $7.5 \times 10^5$ *Staph. aureus* organisms before sodium chlorite treatment has $7.4 \times 10^5$ organisms five minutes after sodium chlorite treatment. Little or no change occurred with *E. coli* or at high concentrations of sodium chlorite.

EXAMPLE 5

This example illustrates how heating the vicinal polyhydroxy compound activates the compound to more effectively catalyze the release of chlorine dioxide from the chlorine dioxide liberating system.

A 1:1 mixture of chlorine dioxide liberating compound (0.6% (w/v) aqueous sodium chlorite solution) and vicinal polyhydroxy compound in a weak organic acid buffer (0.4% (w/v) lactic acid, 9.0% (w/v) dextrose, 3.0% (w/v) 1 N sodium hydroxide) are mixed to form a disinfecting solution. The vicinal polyhydroxy compound in the weak organic acid buffer is prepared by adding the dextrose and sodium hydroxide to water and heating the mixture to 80° C. The mixture is then cooled to room temperature and the lactic acid added.

Additional sodium hydroxide is then added to adjust the pH to 4.5.

In order to characterize the effect that the heating of the vicinal polyhydroxy compound has upon the release of chlorine dioxide from the disinfecting solution, a series of experiments are performed which varies the length of time the vicinal polyhydroxy compound is maintained at an elevated temperature.

In this experiment five identical vicinal polyhydroxy compounds are prepared following the procedure outlined above, with the exception that the dextrose-sodium hydroxide mixture is maintained at 80° C. for 5, 10, 20, 60 and 240 minutes, respectively, prior to the addition of the lactic acid and pH adjustment. The chlorine dioxide liberating compound is then added to the heat activated vicinal polyhydroxy compound and the chlorine dioxide evolution rate measured for 20 minutes following the addition.

The results of this experiment are presented graphically in the FIGURE. The pH values given in the FIGURE represent the pH of the disinfecting solution at 1 minute and 20 minutes following addition of the chlorine dioxide liberating compound. In the absence of heat activation of the vicinal polyhydroxy compound, the release of chlorine dioxide is less than 1.0 ppm 20 minutes following the addition of the chlorine dioxide liberating compound.

It may be seen from the FIGURE that heating the vicinal polyhydroxy compound to 80° C. for 60 minutes produces twice the chlorine dioxide release 20 minutes aftter the addition of the chlorine dioxide liberating compound than is observed for the solution which is heat activated for only 5 minutes. However, heating the vicinal polyhydroxy compound for 240 minutes has no further benefit on the release of chlorine dioxide 20 minutes after the chlorine dioxide liberating compound is added.

One skilled in this art will appreciate that such measurements may be made of any vicinal polyhydroxy compound of the present invention to determine both the optimum heating time and the optimum temperature to activate the release of chlorine dioxide from the chlorine dioxide liberating compounds of the present invention.

Although the foregoing invention has been described, in part, by way of illustration and example for the purposes of clarity and understanding, it will be obvious that certain changes or modifications may be practiced without deviating from the spirit and scope of the invention.

We claim:

1. A process for disinfecting blood fractions, blood components or blood cells not to include red blood cells comprising adding a chlorine dioxide liberating compound to a heat activated saccharide compound in an organic acid buffer to form a disinfecting solution wherein the saccharide compound is activated by heating at a temperature of from about 50° C. to about 150° C. for at least about 1 minute; and adding the disinfecting solution to the blood fractions, blood components or blood cells 2. The process of claim 1 wherein the saccharide compound is heat activated at a temperature of from about 75° C. to about 110° C. for a period of time from about 20 to about 120 minutes.

3. The process of claim 1 wherein the chlorine dioxide liberating compound is selected from the group consisting of alkali metal chlorites and alkaline earth metal chlorites.

4. The process of claim 3 wherein the alkali metal chlorite is sodium chlorite or potassium chlorite.

5. The process of claim 1 wherein the saccharide compound is selected from the group consisting of glucose, galactose, mannose, ribose, rhamnose, and disaccharides thereof.

6. The process of claim 1 wherein the saccharide compound is glucose.

7. The process of claim 1 wherein the organic acid buffer is selected from the group consisting of citric, malic, lactic, mandelic and tartaric acids and salts thereof.

8. The process of claim 1 wherein the saccharide compound in the organic acid buffer comprises an aqueous solution of glucose, lactic acid and sodium hydroxide.

* * * * *